United States Patent [19]

Broger

[11] 4,249,023

[45] Feb. 3, 1981

[54] PROCESS FOR MANUFACTURING TRIPHENYLPHOSPHINE

[75] Inventor: Emil A. Broger, Magden, Switzerland

[73] Assignee: Hoffmann-La Roche Inc., Nutley, N.J.

[21] Appl. No.: 40,950

[22] Filed: May 21, 1979

[30] Foreign Application Priority Data

Jun. 2, 1978 [CH] Switzerland ............... 6071/78

[51] Int. Cl.³ ............................................. C07F 9/50
[52] U.S. Cl. .......................................... 568/17
[58] Field of Search ............... 260/606.5 P; 568/17

[56] References Cited

U.S. PATENT DOCUMENTS

| 3,261,871 | 7/1966 | Fritzsche et al. | 260/606.5 P |
|---|---|---|---|
| 3,280,195 | 10/1966 | Fritzsche et al. | 260/606.5 P |
| 3,405,180 | 10/1968 | Natoli | 260/606.5 P |
| 3,481,988 | 12/1969 | Wünsen | 260/606.5 P |
| 3,751,481 | 8/1973 | Weinberg | 260/606.5 P |
| 3,855,310 | 12/1974 | Chopdekar | 260/606.5 P |

FOREIGN PATENT DOCUMENTS 1618130  5/1971  Fed. Rep. of Germany .... 260/606.5 P

OTHER PUBLICATIONS

Masaki et al., Angew. Chemie 89 558 (1977).

*Primary Examiner*—Helen M. S. Sneed
*Attorney, Agent, or Firm*—Jon S. Saxe; Bernard S. Leon; George W. Johnston

[57] ABSTRACT

A process is disclosed for producing triphenylphosphine in which a triphenylphosphine dichloride-chloroform adduct, obtained by reacting triphenylphosphine oxide with phosgene in chloroform, is reduced with hydrogen. The reduction proceeds in a chloroform solvent or in the absence of a solvent.

9 Claims, No Drawings

4,249,023

PROCESS FOR MANUFACTURING TRIPHENYLPHOSPHINE

BACKGROUND OF THE INVENTION

1. Field of the Invention

This invention relates to triphenylphosphine which is useful in polyene synthesis.

2. Description of the Prior Art

Triphenylphosphine can be recovered by the regeneration of triphenylphosphine oxide resulting from a polyene synthesis.

In a prior art process for recovering triphenylphosphine, triphenylphosphosphine oxide was reacted with phosgene in chloroform to give a triphenylphosphine dichloride-chloroform adduct of the formula $(C_6H_5)_3PCl_2 \cdot CHCl_3$. The adduct was then reduced to triphenylphosphine by heating same with white phosphorous. This prior art process suffered from the disadvantages associated with the use of phosphorous, such as the poisonous nature of phosphorous. Furthermore, when using phosphorous, air must be rigorously excluded.

In another prior art process for recovering triphenylphosphine, triphenylphosphine oxide was reacted (i.e. chlorinated) with phosgene and the resulting triphenylphosphine dichloride was reduced to the desired product. In this prior art process, the chlorination of triphenylphosphine oxide was carried out in a solvent, such as a chlorinated hydrocarbon solvent (e.g. carbon tetrachloride) and the reduction of the resulting triphenylphosphine dichloride was carried out by using hydrogen in toluene. It was of great importance to completely remove the carbon tetrachloride solvent from the triphenylphosphine dichloride obtained in the reaction with phosgene before initiating reduction. The carbon tetrachloride otherwise would react with the triphenylphosphine produced by the reduction and thereby decrease the yield of the desired product. Accordingly, this prior art process disadvantageously compelled the laborious removal of the solvent from the triphenylphosphine dichloride intermediate product.

I have invented a process for producing triphenylphosphine which avoids the disadvantages of the above described prior art processes by utilizing chloroform as the solvent in the chlorination reaction. With the process of the invention, it is no longer necessary to remove the solvent used in the chlorination (adduct forming) step, before initiating the reduction step. I have also found that chloroform is a better solvent than toluene for the reduction of triphenylphosphine dichloride to triphenylphosphine. Methylene chloride and carbon tetrachloride are unsuitable for this reduction (hydrogenolysis).

SUMMARY OF THE INVENTION

The invention concerns a process for producing triphenylphosphine. This compound is a useful reagent in polyene synthesis and can be recovered by the regeneration of triphenylphosphine oxide.

In accordance with the invention, triphenylphosphine oxide is reacted with phosgene in chloroform to form a triphenylphosphine dichloride-chloroform adduct. The resulting adduct is reduced with hydrogen to form the desired triphenylphosphine. The reduction may proceed in chloroform as a solvent or in the absence of a solvent.

DETAILED DESCRIPTION OF THE INVENTION

The invention concerns a process for producing triphenylphosphine.

In accordance with the invention, triphenylphosphine oxide is reacted (e.g., chlorinated) with phosgene in chloroform as a solvent to form a triphenylphosphine dichloride-chloroform adduct. The resulting adduct is reduced with hydrogen in the presence of chloroform as the solvent or alternatively without a solvent.

In a preferred embodiment of the invention, the chlorination of triphenylphosphine oxide with phosgene can be carried out in the presence of about two to about three parts by weight of chloroform per part by weight of triphenylphosphine oxide.

For the chlorination reaction, stoichiometric amounts of triphenylphosphine oxide and phosgene may be used. A slight excess of phosgene is also contemplated by the inventive process.

The temperature for the chlorination reaction is not particularly critical, and the reaction is conveniently carried out at room temperature (about 20° C. to about 25° C.).

The reaction time for the chlorination is normally about ½ to about 2 hours.

The triphenylphosphine dichloride-chloroform adduct obtained in the chlorination reaction is filtered off, washed with chloroform and suspended while in its moist condition (without previous drying) in chloroform. The adduct then is reduced to the desired triphenylphosphine. Alternatively, the adduct can be filtered off from the reaction mixture and reduced directly, in the absence of a solvent, to triphenylphosphine. Further, the reaction mixture obtained in the chlorination reaction can be directly reduced to triphenylphosphine without the aforementioned filtering or washing. The reduction is preferably effected in the presence of small amounts, e.g. up to 5 mol% of phosgene.

In accordance with the invention, the reduction of the triphenylphosphine dichloride-chloroform adduct conveniently is carried out with hydrogen under pressure. The pressure may be about 10 to about 300 bar, conveniently about 10 to about 100 bar and preferably about 100 bar.

The temperature employed in the reduction is normally at least about 130° C., conveniently about 160-220° C. and preferably about 190-195° C.

The reaction time for the reduction depends on the pressure and the temperature and is, in general, between about a few minutes and about several hours.

The reduction is conveniently carried out with an about 5 to about 75% by weight solution of triphenylphosphine dichloride in chloroform. Preferably the reduction occurs in an about 10 to about 20% by weight solution of triphenylphosphine dichloride in chloroform.

The reaction vessel used for the reduction conveniently has an internal lining of glass, Teflon coating (manufactured by E. I. Dupont), tantalum or platinum.

The process of the invention can be carried out batchwise or continuously.

In a preferred embodiment of the present process for producing triphenylphosphine, about 1 part by weight of triphenylphosphine oxide in about 2 to about 3 parts by weight of chloroform is chlorinated with phosgene to produce a triphenylphosphine dichloride-chloroform adduct solution. The solution is adjusted (concentrated or diluted) by a known procedure to one having about 10 to about 20% by weight triphenylphosphine dichloride-chloroform adduct in chloroform. The resulting solution is hydrogenated at a pressure of about 100 bar of hydrogen and at a temperature of about 190° C. to about 195° C. to form the desired triphenylphosphine.

The following non-limiting examples further illustrate the invention. Unless otherwise stated, temperatures are in degrees Celsius (°C.).

EXAMPLE 1

A solution of 52 g of phosgene in 100 ml of chloroform is added dropwise at 20° over 2 hours to a solution of 139 g of triphenylphosphine oxide in 150 ml of chloroform. The resulting suspension is stirred at 20° for 1 hour and then at 0° for 1 hour. The triphenylphosphine dichloride-chloroform adduct [$(C_6H_5)_3PCl_2 \cdot CHCl_3$] formed is filtered off and washed with chloroform. The resulting moist product is suspended in 1 liter of chloroform and hydrogenated in a glass lined autoclave at 180° and 100 bar of hydrogen for 1 hour. The reaction solution is evaporated and the residue is recrystallized from ethanol. Yield, 106 g of triphenylphosphine, m.p. 80–81°. The triphenylphosphine and triphenylphosphine oxide in the mother liquor is recycled.

EXAMPLE 2

18.1 g of triphenylphosphine dichloride-chloroform adduct are hydrogenated at 180° and 100 bar of $H_2$ for 1 hour. Yield 8.2 g of triphenylphosphine.

EXAMPLE 3

18.1 g of triphenylphosphine dichloride-chloroform adduct are hydrogenated in 100 ml of chloroform at 160° and 20 bar of $H_2$ for 9 hours. Yield 8.8 g of triphenylphosphine.

EXAMPLE 4

A suspension of 18.1 g of triphenylphosphine dichloride-chloroform adduct in 50 ml of chloroform is hydrogenated at 180° and 20 bar of hydrogen for 3 hours. Yield 9.0 g of triphenylphosphine.

EXAMPLE 5

A suspension of 181 g of triphenylphosphine dichloride-chloroform adduct in 1 liter of chloroform is heated to 190° under 20 bar of nitrogen. Then, 100 bar of hydrogen are forced therein and the resulting mixture is hydrogenated at 190–195° for 15 minutes. Yield 93.3 g of triphenylphosphine.

EXAMPLE 6

A suspension of 18.1 g of triphenylphosphine dichloride-chloroform adduct and 1 ml of phosgene in 90 ml of chloroform is hydrogenated at 90 bar of hydrogen and 180° for 1 hours. The resulting solution is evaporated and the residue is chromatographed on silica gel. 10.1 g of triphenylphosgene, m.p. 80–81°, are eluted with benzene.

EXAMPLE 7

90.5 g of triphenylphosphine dichloride-chloroform adduct is hydrogenated in 500 ml of chloroform at 140° and 100 bar of hydrogen for 9 hours. Yield 43.5 g of triphenylphosphine.

We claim:

1. A process for producing triphenylphosphine which comprises:
   (a) reacting triphenylphosphine oxide with phosgene in chloroform to produce a triphenylphosphine dichloride-chloroform adduct; and
   (b) reducing said triphenylphosphine dichloride-chloroform adduct with hydrogen at a temperature of at least about 130° C. in the presence of chloroform as the solvent or in the absence of a solvent, to give triphenylphosphine.

2. The process of claim 1 wherein the reaction of triphenylphosphine oxide with phosgene is carried out in the presence of about 2 to about 3 parts by weight of chloroform per part of triphenylphosphine oxide.

3. The process of claims 1 or 2 wherein said adduct is adjusted to about 5 to about 75% by weight of triphenylphosphine dichloride before it is reduced.

4. The process of claim 3 wherein said adduct is adjusted to about 10 to about 20% by weight of triphenylphosphine dichloride before it is reduced.

5. The process of claim 1 or 2 wherein the reduction is carried out at a temperature of about 160° C. to about 220° C.

6. The process of claim 5 wherein the reduction is carried out at a temperature of about 190° C. to about 195° C.

7. The process of claims 1 or 2 wherein the reduction of said triphenylphosphine dichloride-chloroform adduct is carried out in the presence of up to about 5 mol% of phosgene.

8. The process of claims 1 or 2 wherein the reduction is carried out at a pressure of from about 10 to about 100 bar of hydrogen.

9. A process for producing triphenylphosphine comprising reducing a triphenylphosphine dichloride-chloroform adduct with hydrogen at a temperature of at least about 130° C. in the presence of chloroform as the solvent or in the absence of any solvent to give triphenylphosphine.

* * * * *